United States Patent [19]

Schaller née Kornmayer et al.

[11] Patent Number: 4,457,917

[45] Date of Patent: Jul. 3, 1984

[54] PEPTIDE, PROCESS FOR ITS PREPARATION AND PHARMACEUTICAL COMPOSITION CONTAINING SAME

[75] Inventors: Hildegard C. Schaller née Kornmayer, Heidelberg; Heinz Bodenmüller, Ludwigshafen, Fed. Rep. of Germany

[73] Assignee: Max-Planck-Gesellschaft zur Foerderung der Wissenschaften e.V., Gottingen, Fed. Rep. of Germany

[21] Appl. No.: 374,554

[22] Filed: May 3, 1982

[30] Foreign Application Priority Data

May 6, 1981 [DE] Fed. Rep. of Germany ....... 3117934

[51] Int. Cl.³ .................... A61K 37/02; C07C 103/52
[52] U.S. Cl. ............................. 424/177; 260/112.5 R
[58] Field of Search ................. 424/177; 260/112.5 R

[56] References Cited

PUBLICATIONS

Bodenmüller et al., *Nature,* 293, 579–580, Oct. 15, 1981.

*Primary Examiner*—Delbert R. Phillips
*Assistant Examiner*—F. T. Moezie
*Attorney, Agent, or Firm*—Felfe & Lynch

[57] ABSTRACT

The new compound pGlu-Pro-Pro-Gly-Gly-Ser-Lys-Val-Ile-Leu-Phe is a neuropeptide which is of interest as a research substance and pharmaceutical composition. Its preparation is performed synthetically by conventional methods of peptide synthesis, or by extracting animal tissue with an organic solvent and purifying the extract by chromatography through ion exchangers and through slightly crosslinked molecular sieve columns, and by high-pressure liquid chromatography.

2 Claims, No Drawings

PEPTIDE, PROCESS FOR ITS PREPARATION AND PHARMACEUTICAL COMPOSITION CONTAINING SAME

The invention relates to a previously unknown peptide of 11 amino acids, a process for its preparation, and its use in pharmaceutical compositions.

The peptide of the invention consists of 11 amino acids and has the following sequence:

pGlu-Pro-Pro-Gly-Gly-Ser-Lys-Val-Ile-Leu-Phe.

The sequence given above has been confirmed by synthesis.

The peptide of the invention has the following retention times on a reversed phase octylsilane column (LiChrosorb RP-8, particle size 7 μm, column size 250×4 mm) at a rate of flow of one milliliter per minute:

1. in 50% methanol in 5 mM of ammonium bicarbonate, isocratic, 7.6 min.
2. with gradient (10 min) from 40 to 60% methanol in 5 mM of ammonium bicarbonate, 10.5 min.
3. in 30% acetonitrile in 0.1% TFA (trifluoroacetic acid), isocratic, 8 min.
4. with gradient (10 min) from 20 to 40% acetonitrile in 0.1% TFA, 11.2 min.

The peptide of the invention is the active substance of the so-called "head activator". In the case of Hydra, the compound acts as a mitogen, where it is necessary for the cell division of all types of cells. In Hydra, the compound is also responsible for head-specific determination, i.e., an interstitial parent cell is determined by the connection to the nerve cell. These effects occur at very low concentrations of the order of $10^{-10}$ M. On mammals the compound has a growth-stimulating action on embryonal brain cells and has a hypertensive (pressor) effect upon intraventricular administration. On the basis of its biological properties, the compound of the invention is an interesting research chemical and furthermore offers interesting possibilities for its use as a pharmaceutical.

It has been found that the compound of the invention can be obtained from animal tissues, especially from the hypothalamus region of the brain or from the intestine of mammals or from whole coelenterates. The process of the invention for its preparation is characterized by the fact that the animal tissue is extracted with an organic solvent (such as acetone, acetic acid or methanol), centrifuged, and the concentrated (e.g., by ultrafiltration) extract is purified by chromatography through ion exchangers (e.g., weakly acid anionic or weakly basic cationic exchangers) and through slightly cross-linked molecular sieve columns (e.g., dextran or polyacrylamide), and the fractions containing the desired peptide are then subjected to high-pressure liquid chromatography (e.g., through reversed phase octyl or octadecasilyl columns). From a human hypothalamus this process produces approximately one nanomole of the compound. By preparing the compound from the amino acids by conventional methods of peptide synthesis, the compound can easily be obtained in any desired amount.

The synthesis of the compound of the invention can be performed by any peptide synthesis method, e.g., by Merrifield's method of solid phase synthesis with symmetrical anhydrides (Hoppe Seyler's Z. Physiol. Chem. 353, 1973-1976 (1972) or in the liquid phase with mixed anhydrides (Liebigs Ann. Chem. 572, 190-194 (1951) with or without the use of automatic peptide synthesis apparatus.

Synthesis through the cloning of the coding nucleic acid is also possible.

As the formula shows, the compound contains two molecules each of proline and glycine as well as one molecule of each of 7 other amino acids. A peculiarity that is characteristic of many peptide hormones is the presence of a pyroglutamic acid at the amino terminus. The molecule is characterized by a strong hydrophobicity in the carboxy terminal portion.

In the process of production from animal starting material, the latter is comminuted as finely as possible in the organic solvent (methanol, for example) while maintaining a low temperature not to exceed 10° C. After centrifugation, the concentrated supernatant is washed with petroleum ether and chloroform to separate lipids. The chromatography steps that follow are performed preferably at a neutral pH. Optionally, the process can be preceded by treatment with a slightly basic anion exchanger, such as a crosslinked dextran bearing diethylaminoethyl groups, in which case the compound of the invention is bound in the case of 5 mM of ammonium acetate at pH <7.5 and eluted again at pH <3.5. The commercially obtainable product known as Sephadex G-10 has proven especially desirable for use as the slightly crosslinked dextran gel on account of its unusual adsorption properties. The product that is commercially obtainable under the name Biogel P2 has proven to be especially well suited as the polyacrylamide gel. However, other dextran gels and polyacrylamide gel preparations can be used which have comparable properties, especially as regards the degree of crosslinking.

The elution is performed with dilute salt solution, such as 0.1 M NaCl, for example. The desired pH in the above-stated range can be adjusted with any buffer substance. Tris buffer is preferred.

Reversed phase octylsilane, which is commercially obtainable under the name "LiChrosorb RP-8" is preferred for the high-pressure liquid chromatography. The compound of the invention is retained on this support material under polar conditions (little organic component, such as methanol or acetonitrile, for example, in the mobile phase), and it is eluted under apolar conditions (much organic component in the mobile phase).

The synthetic preparation of the compound of the invention can be performed, as mentioned above, by conventional methods of protein synthesis. The pyroglutamic acid group at the amino terminal can be formed by insertion, for example, the insertion of glutamine followed by cyclization by heating in acid (TFA, for example).

On the basis of the above-described properties of the new compound of the invention, this neuropeptide, which first occurs in the animal kingdom and has strictly preserved its structure down to the human kind, is an interesting research substance and can be used as an active substance in pharmaceutical preparations for the regulation of growth and/or as a transmitter substance.

The following examples further explain the invention:

EXAMPLE 1

10 to 13 kg of deep-frozen *Anthopleura elegantissima*, Pacific Biomarine Laboratories, California, is chopped into small pieces of 1 to 3 cm, cold methanol ($-20°$ C.)

is added until the pieces are well covered (approximately 1 part pieces to 2 parts methanol). The mixture is homogenized (Ultraturax). The temperature is not to exceed 10° C. (cool with an ice bath, technical NaCl or cattle salt). The homogenates are centrifuged for 10 minutes at 2000 rpm (prechill rotor and centrifuge, and run at 4° C.). The supernatants are collected and kept at −20° C. The sediments are mixed with cold methanol (−20° C.) in the centrifuge beaker, and the homogenization and centrifugation are repeated twice. The combined supernatants are concentrated in the rotary evaporator to 10 to 15 liters and shaken with cold petroleum ether. The petroleum ether phase is discarded. The washing is repeated until the green color is in the ether. The washed solution is extracted thrice with cold chloroform, and the first chloroform phase is also washed once. The collected aqueous phases are concentrated to a very small volume (rotary evaporator), frozen and dried.

The freeze-dried concentrate is dissolved with a minimal amount of methanol and centrifuged, and the supernatant is separated. The sediment is again extracted with methanol and centrifuged. The collected supernatants are evaporated, dissolved in distilled water (total volume about 500 ml), adjusted to pH 7.6, and applied in amounts of 250 ml to a Sephadex G-10 column (5.3 l total capacity, 10×73.5 cm).

Alternatively, for each 500 ml of extract 100 g of Sephadex DEAE-A-25 is balanced overnight with 5 mM of $NH_4Ac$, pH 7.6, shaken with the supernatant for 30 minutes and centrifuged for 30 minutes at 1500 rpm. The supernatant is placed on fresh DEAE (100 g), and this is repeated until no more color binds to the DEAE Sephadex (normally 3 to 4 times). The DEAE Sephadex is eluted with 5 mM of $NH_4Ac$, pH 3.5, until there is no more color in the supernatant. The eluate is neutralized, concentrated by evaporation, and placed in batches of 25 ml on a Sephadex G-10 column (total volume 250 ml, 5.5.×13 cm), and chromatographed with distilled water.

Then the fractions 9.5 to 14.5 l of the 5.3 l G-10 column, or the fractions 500 to 1000 ml of the 250 ml G-10 column, are concentrated to 20 ml and placed on an acrylamide gel column (Biogel P-2; 660 ml, 4.5×50 cm) and eluted with 5 mM of ammonium bicarbonate solution. The fractions 300 to 450 ml are combined, concentrated to 1 ml, and placed on another G-10 column (volume 25 ml, 1.5 ×16 cm) and eluted with 0.1 M NaCl, 0.01 M tris-HCl, pH 7.6. The combined fractions 29 to 42 ml are concentrated to 1 ml and placed on an acrylamide gel column (Biogel P-2 40 ml, 1.3×47 cm) and eluted with the same eluent as in the preceding step.

The active fractions are combined, concentrated to 0.5 ml and placed in a Pasteur capillary pipette containing 0.5 ml of LiChrosorb RP-8, particle size 10 μm, which is balanced with 20% methanol in 5 mM of ammonium bicarbonate. After washing with the balancing agent, elution is performed with 3 ml of 80% methanol in 5 mM of ammonium bicarbonate solution, the eluate is dried, redissolved in 0.1% TFA, and the treatment in the Pasteur capillary pipette is repeated, except that the eluent is 3 ml of 40% acetonitrile in 0.1% TFA. The eluate is concentrated and placed on a high-pressure liquid chromatography column (LiChrosorb RP-8, particle size 7 μm, 250×4 mm) which has been balanced with 20% acetonitrile in 0.1% TFA, and eluted for 10 minutes with a gradient up to 40% acetonitrile in 0.1% TFA, at a rate of flow of 1 ml/min. The retention time of the compound of the invention amounts to 10.6 minutes.

The eluate is concentrated to 50 μl and again placed on the same kind of high-pressure liquid chromatography column, which has been balanced with 40% methanol in 5 mM of ammonium bicarbonate and it is eluted with a gradient up to 60% methanol for 10 minutes, rate of flow 1 ml/min. The retention time of the compound of the invention amounts to 10.5 minutes. One nanomole of pure compound is thus obtained.

EXAMPLE 2

1000 rats (2 to 3 months old) are narcotized with $CO_2$, the abdominal wall was opened and the intestine without the pancreas, from the pylorus to the last intestinal thickening before the anus, was removed and prepared. The intestines are collected in 20 liters of cold methanol, 0.05% phenylmethylsulfonylfluoride is added and then the mixture is further processed as described in Example 1. Ten nanomoles of the compound of the invention are obtained.

EXAMPLE 3

A human hypothalamus (20 h after death) was homogenized at 4° C. with excess methanol and then twice treated for 2 minutes with ultrasound. By centrifugation a supernatant was obtained which, after concentration, was washed with petroleum ether and with chloroform. After re-extraction with water as described in Example 1, the aqueous phase was concentrated to 10 ml and placed on a Sephadex G-10 column of 250 ml volume, and eluted, as described in Example 1. The fraction 500 to 1000 ml was concentrated and applied directly to a LiChrosorb RP-8 column of 0.5 ml. Further purification is performed as in the final steps of Example 1. One nanomole of the compound of the invention is obtained.

We claim:
1. pGlu-Pro-Pro-Gly-Gly-Ser-Lys-Val-Ile-Leu-Phe.
2. A pharmaceutical composition for cell-growth stimulating action comprising an effective amount of the compound of claim 1 as active substance together with conventional pharmaceutical carrier.

* * * * *